United States Patent [19]
Gresl, Jr.

[11] 3,972,812
[45] Aug. 3, 1976

[54] BLOOD SERUM SEPARATION FILTER DISC
[75] Inventor: Charles Gresl, Jr., Fairfield, N.J.
[73] Assignee: Becton, Dickinson and Company, Rutherford, N.J.
[22] Filed: May 8, 1975
[21] Appl. No.: 575,740

[52] U.S. Cl. ................................ 210/77; 128/272; 210/83; 210/359; 210/DIG. 23
[51] Int. Cl.² ........................................ B01D 21/26
[58] Field of Search ............... 23/230 B, 258.5, 259, 23/292; 128/2 F, 214 R, 218 M, 272, DIG. 5, DIG. 28; 210/83, 84, 77, 359, 514–518, DIG. 23, DIG. 24; 233/1 A, 1 R, 26

[56] References Cited
UNITED STATES PATENTS

| | | | |
|---|---|---|---|
| 1,995,072 | 3/1935 | Mills | 210/516 |
| 3,508,653 | 4/1970 | Coleman | 210/83 |
| 3,647,070 | 3/1972 | Adler | 210/83 |
| 3,870,639 | 3/1975 | Moore et al. | 210/359 |
| 3,873,449 | 3/1975 | Connelly et al. | 210/359 |
| 3,926,646 | 12/1975 | Adler | 210/359 |
| 3,931,018 | 1/1976 | North, Jr. | 210/359 |

*Primary Examiner*—Charles N. Hart
*Assistant Examiner*—R. G. Mukai
*Attorney, Agent, or Firm*—Kane, Dalsimer, Kane, Sullivan and Kurucz

[57] ABSTRACT

An impregnated porous disc made of an inert material with voids adapted for insertion into a collection tube containing clotted blood which disc upon centrifugation of the tube will allow separation of fibrin and cellular material from the serum by centrifugal force during its controlled descent through the serum and will stop when it hits the serum-clot interface to isolate the serum from the clot.

14 Claims, 3 Drawing Figures

BLOOD SERUM SEPARATION FILTER DISC

BACKGROUND OF THE INVENTION

1. Field of the Invention

The invention concerns devices and apparatus for isolating blood serum from coagulated whole blood and blood plasma from mixtures of whole blood with anti-coagulants.

2. Description of the Prior Art

Prior hereto the most widely employed apparatus for separating the liquid phase components from the solid phase components of a blood mixture utilized centrifugation of the mixture. The serum or plasma is generally then isolated from the solid portion by pipette or decantation techniques. In general, this method does not entirely separate all of the solid particulate matter from the desired serum or plasma. When the serum is to be subjected to a diagnostic analysis with, for example, an automated electronic analyzer it is important to employ a particulate-free specimen. Fibrin fibers are often the cause of analyzer malfunctions when they clog conduits or orifices in the analyzer.

Illustrative of the prior art blood component separation devices are those described in U.S. Pat. Nos. 3,481,477; 3,512,940 and 3,693,804. Although such separation devices do isolate the desired blood serum or blood plasma, they are relatively expensive to construct, requiring extremely close tolerances and seals for operation. They have not been heretofore as widely accepted commercially as the need suggests, because of their cost and difficulty to manufacture. In addition, the prior art separation devices such as those described in the above patents operate in part by exerting force or pressure upon the blood mixture to be separated. If too great a force is imposed upon the blood mixture, there is a danger that the serum or plasma will pass through the devices with sufficient velocity to force small particles of solid material through the orifices, particularly a resilient filter. The velocity of the filtrate leaving the filter member may also be sufficient to "spray" the filtrate out of the collector device. Furthermore, the necessary force must be applied manually, and only one or two specimens may be processed simultaneously, which is an inefficient use of labor. The isolation procedure with the prior art devices are also generally carried out following separation of the blood components by centrifugation, thereby requiring two distinct steps with consequent extension of time required for total serum preparation.

In contrast, the device and apparatus of my invention is relatively simple and is activated by readily available and self-limiting gravitational forces. Thus, it enables one to carry out separation and isolation of the desired blood serum or blood plasma in one convenient centrifugation step. The device is readily applied to a large number of specimens simultaneously, and the centrifugation step is the same operation widely employed in separating serum from clotted blood and cells from mixtures of blood with anti-coagulants. Likewise, the apparatus of my invention is extremely simple in construction and is readily manufactured at low cost since it does not require close dimensional tolerances or seals. The device and apparatus of my invention are particularly useful in the separation of blood serum from clotted whole blood.

SUMMARY OF THE INVENTION

The invention relates to a device for the simultaneous isolation during separation of the liquid phase of blood from the substantially cellular phase thereof which comprises: an impregnated porous disc or plug made of an inert material with voids adapted for insertion into a blood collection tube containing whole blood which disc upon centrifugation will form a barrier in the liquid phase during its controlled descent through such liquid phase and come to a stop when it hits the interface between the liquid and cellular phases to isolate such phases from each other.

The invention also comprises unitary, self-contained assemblies for the separation of blood serum and plasma from whole blood which employ the device of the invention as a component thereof.

DESCRIPTION OF THE PREFERRED EMBODIMENT

Figure 1:
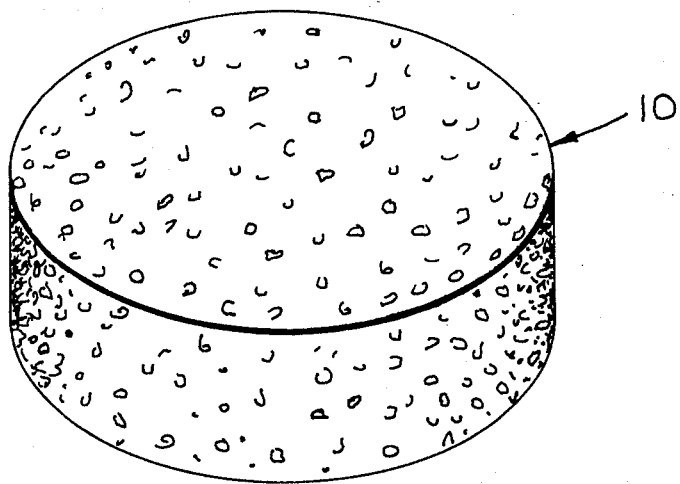
FIG. 1 is a perspective view of the filter disc of the present invention.

The device which should be used to form the barrier between serum and clot to aid decanting should descend through the serum after the clot has spun down in order to provide the optimum quality of serum. When using a porous disc which is placed on top of the clotted blood in a tube, one means of retarding the descent of the filter disc to the clot is to control the time required for the filter disc to pass through the air-serum interface.

The factors which control the rate of descent through the air-serum interface are the following properties of the porous disc; Mass, Specific Gravity, Percent Void Volume, Pore Size and Wettability. The descent time can be increased on a given material by coating or treating the filter disc so as to make the surface of the material hydrophobic. By decreasing the wettability of the porous material, the serum flows more slowly into the porous disc under the action of the force field of the centrifuge. The disc will not sink in the serum until a sufficient quantity of the air in the void volume of the porous material is displaced by serum, negating the buoyant effects of the air.

The porous disc 10 of the present invention is made of an inert material, which means it will have no detrimental effects on the blood or serum sample which would result in an analysis which would differ from that made on the same sample if the device was not used. The porous disc material has a pore size of about 70 to 300 microns. The density is greater than that of serum (i.e. >1.03 SpG) so that the filter disc descends to the serum/clot interface. The density should not exceed the density of the clot (i.e. <1.09 SpG) in order to eliminate pressure on the clot which displaces and hemolyzes red cells. The required specific gravity of the disc can be achieved by using fillers, for example, talc, glass and silica, where the specific gravity of the virgin polymer is too low.

The dimensions of the cylindrical filter disc are controlled so that the diameter and length of the disc relative to that of the collection tube effectively prevents passage of unwanted blood constituents from the clot side to the serum side of the filter. Flow around the disc during serum pour off is prevented by the surface tension of the serum in the gap between the glass and porous plug. In addition, the diameter of the filter disc is such that it can be readily inserted in the blood collection tube and will move freely due to the forces developed during centrifugation. Also, the height of the filter assures proper insertion into the blood tube to maintain the filter disc surface parallel to the upper surface of the clot and to provide the correct void volume.

The filter disc 10 is in the form of a cylindrical plug and can be made of a general polymeric material, such as sintered nylon, styrene, polyethylene and polypropylene. The diameter will vary according to the tube into which it is to be placed. For example in a tube having a diameter of 0.430 inches the disc would be approximately 0.410 inches with a height of about 0.250 inches.

Such disc is sprayed with a material to make the surface of the material hydrophobic, for example Silanox 101 spray (1% dispersion of fumed silicon dioxide in isopropyl alcohol and propellant with 0.7% resin binder), dimethyl silicone oil, silane, mineral oil and wax and dried.

To illustrate how the descent time has been increased by the coating or impregnation of the filter disc the following tests were run:

Two test tubes approximately 0.430 inches in diameter were filled to equal levels with blood serum. An untreated porous nylon disc was dropped in one tube and a Silanox 101 treated disc was dropped in the other tube. The tubes were then spun in a centrifuge and observed to measure the times the discs stayed afloat. Such times were as follows:

Time to sink using Dynac centrifuge:
   Untreated — 6 seconds at 2400 rpm
   Treated — 5 minutes at 2400 rpm plus 1 minute at 3000

It will thus be apparent that the treated disc floated for a considerably longer time than the untreated disc.

Figure 2:
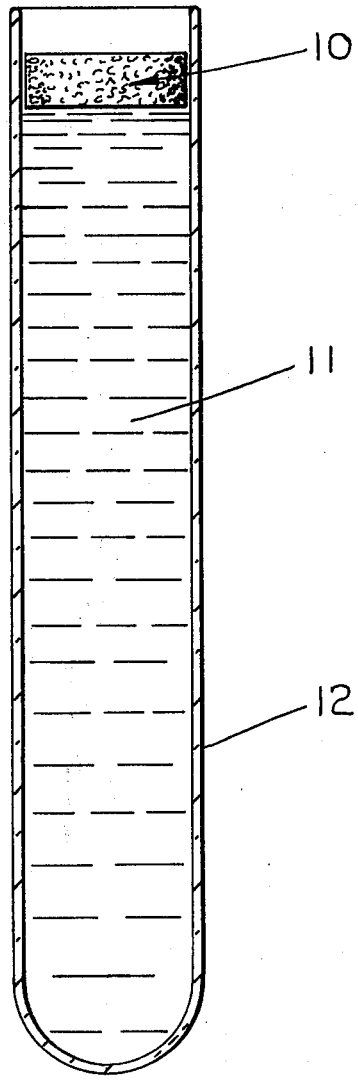
FIG. 2 is a cross-sectional side elevation of the disc in use, prior to the separation of the liquid phase of the blood specimen.
Figure 3:
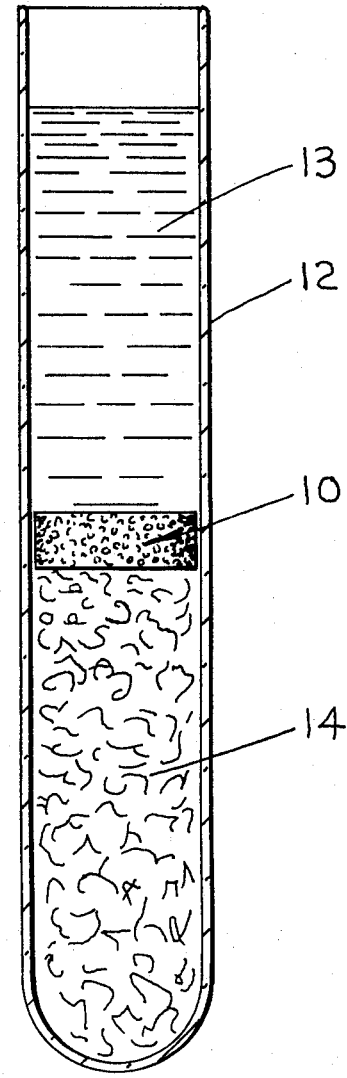
FIG. 3 is a view similar to FIG. 2, but following separation of the blood specimen.

In using the filter disc of the present invention the following procedure is followed:

Whole blood 11 was collected in a tube 12, such as a Becton Dickinson Vacutainer, and left in a test tube rack for 1 hour to clot. After 1 hour the stopper was removed and the mouth of the tube was swabbed to remove clotted blood left by the stopper. The filter disc 10 was inserted into the open end of the tube (FIG. 2).

The tube was then spun in a Clay Adams Dynac centrifuge for 10 minutes at 2400 RPM in a normal manner to separate serum from the clot. The filter disc descended to the level of the serum clot interface and remained in this position isolating the serum 13 from the clot 14. Examination upon removal showed the serum and the top face of the filter disc to be free of red cells.

When the tube was inverted, the serum poured off, and the filter disc and clot remained in the tube. The upper section of the filter was free of red cells or hemolyzed cell material. Thus it will be seen, the disc formed a mechanical barrier which aided in decanting the serum. In addition, this depth type filter served to retard the diffusion of undesirable constituents in the clot (such as hemolyzed red blood cells) into the serum if the serum is not immediately decanted after separation.

Thus, among others, the several aforenoted objects and advantages are most effectively attained. Although a somewhat preferred embodiment of the invention has been disclosed and described in detail herein, it should be understood that this invention is in no sense limited thereby and its scope is to be determined by that of the appended claims.

Having thus described the invention, what is claimed is:

1. A separation device for insertion into a tubular container for isolating the lighter components from the heavier components of blood mixtures selected from coagulated whole blood and mixtures of whole blood with anti-coagulants comprising:
   a cylindrical disc made of an inert porous polymeric material having a pore size of about 70 to 300 microns, the said disc having a diameter sized to form a sliding fit with the inner wall of the tubular container and a height sized to maintain the disk coaxial with respect to the tubular container;
   said disc being coated with a hydrophobic material to make the surfaces of the porous material of the disc hydrophobic to increase the descent time of the disc through the soluble components;
   said coated disc having a specific gravity such that it will sink in said lighter components but will not sink in said heavier components.

2. The device of claim 1 wherein said disc is sintered nylon.

3. The device of claim 1 wherein said disc is styrene.

4. The device of claim 1 wherein said disc is polyethylene.

5. The device of claim 1 wherein said disc is polypropylene.

6. The device of claim 1 wherein said disc is coated with a 1% dispersion of fumed silicon dioxide in isopropyl alcohol and propellant with 0.7% resin binder.

7. The device of claim 1 wherein said disc is coated with dimethyl silicone oil.

8. The device of claim 1 wherein said disc is coated with silane.

9. The device of claim 1 wherein said disc is coated with mineral oil.

10. The device of claim 1 wherein said disc is coated with wax.

11. The device of claim 1 wherein said coated disc has a specific gravity of between about 1.03 to 1.09.

12. The device of claim 1 wherein said coated disc has pore sizes of about 70 to 300 microns.

13. An assembly for the separation of the liquid portion of whole blood from the substantially cellular portion thereof which comprises:
   a tubular container; and
   a separation device which comprises:
     a. a cylindrical disc made of an inert porous polymeric material having a pore size of about 70 to 300 microns, the said disc having a diameter sized to form a sliding fit with the inner wall of the tubular container and a height sized to maintain the disk coaxial with respect to the tubular container;
     b. said disc being coated with a hydrophobic material to make the surfaces of the porous material of the disc hydrophobic to increase the descent time of the disc through the liquid portion; and
     c. said coated disc having a specific gravity such that it will sink in said liquid portion but will not sink in the cellular portion of the blood;

whereby upon centrifugation of the tubular container containing whole blood the barrier device will come to a stop at the interface between the liquid and cellular portions to isolate such portions from each other.

14. In the method of separating a blood mixture in a blood collection tube into its liquid phase and cellular phase components by emplacement under centrifugal force of a disc at the interface between the said components the improvement which comprises providing a disc which is cylindrical and made of an inert porous polymeric material having a pore size of about 70 to 300 microns, said disc having a diameter sized to form a sliding fit with the inner wall of the collection tube and a height sized to maintain the disk coaxial with respect to the collection tube, said disc is coated with a polymeric hydrophobic material to make the surfaces of the porous material of the disc hydrophobic to increase the descent time of the disc through the liquid components, and said coated disc having a specific gravity such that it will sink in said liquid components but will not sink in said cellular components.

* * * * *